(12) United States Patent
Yamagami et al.

(10) Patent No.: US 7,959,939 B2
(45) Date of Patent: Jun. 14, 2011

(54) LAMINATE OF CULTURED HUMAN CORNEAL ENDOTHELIAL CELLS LAYER AND METHOD FOR MANUFACTURING SAME

(75) Inventors: Satoru Yamagami, Saitama (JP); Tatsuya Mimura, Tokyo (JP); Shiro Amano, Tokyo (JP); Keisuke Tanaka, Tokyo (JP); Shunji Hattori, Tokyo (JP); Shinkichi Irie, Tokyo (JP); Yasuhiro Osakabe, Tokyo (JP)

(73) Assignees: Satoru Yamagami, Saitama (JP); Tatsuya Mimura, Tokyo (JP)

( * ) Notice: Subject to any disclaimer, the term of this patent is extended or adjusted under 35 U.S.C. 154(b) by 1002 days.

(21) Appl. No.: 10/590,184

(22) PCT Filed: Feb. 17, 2005

(86) PCT No.: PCT/JP2005/002402
§ 371 (c)(1), (2), (4) Date: Jun. 13, 2007

(87) PCT Pub. No.: WO2005/078071
PCT Pub. Date: Aug. 25, 2005

(65) Prior Publication Data
US 2007/0238173 A1    Oct. 11, 2007

(30) Foreign Application Priority Data
Feb. 18, 2004 (JP) .................................. 2004-041874

(51) Int. Cl.
*A61F 2/00* (2006.01)
(52) U.S. Cl. ....... 424/423; 424/427; 424/460; 424/93.7; 514/9.3; 623/5.16; 435/325; 435/384
(58) Field of Classification Search ........................ None
See application file for complete search history.

(56) References Cited

U.S. PATENT DOCUMENTS
5,716,633 A * 2/1998 Civerchia ...................... 424/428

FOREIGN PATENT DOCUMENTS

| | | |
|---|---|---|
| JP | 2002-078723 | 3/2002 |
| JP | 2003-038170 | 2/2003 |
| JP | 2004-024852 | 1/2004 |
| JP | 2004-298447 | 10/2004 |
| WO | WO 94/10940 A1 | 5/1994 |
| WO | WO 96/13974 | 5/1996 |
| WO | WO 2004/069295 A1 | 8/2004 |
| WO | WO 2005/037144 | 4/2005 |

OTHER PUBLICATIONS

Newsome et al., Invest. Ophthalmol. Vis. Sci.,1982, vol. 22, p. 376-381.*
Miyata et al., Cornea, 2001, vol. 20. No. 1, p. 59-63.*
Inoue et al., Invest. Ophthalmol. Vis. Sci., 1993, vol. 34, No. 7, 2313-2315.*
Amano et al., 2002, Journal of Japanese Ophthalmologic Society, vol. 106, No. 12, p. 805-836.*
Inoue et al., Invest. Ophthalmol. Vis. Sci., 1993, vol. 34, No. 7, 2313-2315.*
PCT/JP2005/002402, International Preliminary Report on Patentability, Sep. 28, 2006.
Shiro, Abstract of "Transplantation of corneal endothelial cells", Nippon Ganka Gakkai Zasshi, Dec. 2002, Abstract XP-002312237.
Kobayashi et al., "Collagen-Immobilized Hydrogel as a material for Lamellar Keratoplasty", Journal of Applied Biomaterials, Vo. 2, No. 4, Jan. 1991, pp. 261-267.
Mimura et al., "Cultured Human Corneal Endothelial Cell Transplantation with a Collagen Sheet in a Rabbit model", Investigative Ophthalmology & Visual Science, vol. 45, No. 9, Sep. 2004, pp. 2992-2997, XP003000760.
Shiro Amano et al., "Me no Saisei Igaku, Kakumaku Naihi Saibo Ishoku", Journal of Japanese Ophthalmological Society (2002), vol. 106, No. 12, pp. 805 to 836.

* cited by examiner

*Primary Examiner* — Kade Ariani
(74) *Attorney, Agent, or Firm* — Ditthavong Mori & Steiner, P.C.

(57) ABSTRACT

A laminate comprising a transparent collagen I type sheet and a human corneal endothelial cell culture layer provided on the sheet. An endothelial cell culture layer laminate usable in transplantation is provided.

17 Claims, 6 Drawing Sheets

LAMINATE OF CULTURED HUMAN CORNEAL ENDOTHELIAL CELLS LAYER AND METHOD FOR MANUFACTURING SAME

TECHNICAL FIELD

The present invention relates to a laminate of cultured human corneal endothelial cells layer and a method for manufacturing the same.

BACKGROUND TECHNOLOGY

Corneal endothelial cells (CECs) play a highly important role in maintaining transparency of the cornea. However, CECs are said to proliferate and regenerate little in an organism (the human body). When CECs are injured, the injured area does not fill with proliferating cells; instead, the injury heals by a mechanism where the surface area of the cells is increased to fill the gap through the extensional migration and compensatory expansion of cells. As a result, the density of CECs per unit of surface area decreases. Accordingly, for example, when the injury heals through expanding the surface area of CECs, functioning of the cornea is self-limiting; when torn, disorders such as bullous keratopathy result. In that case, the conventional treatment has been a cornea transplant. However, in Japan at least, there is an acute shortage of cornea donors. There is also the problem of tissue compatibility when conducting a transplant. Treatment by corneal transplant is thus far from being an ideal solution.

Figure 8:
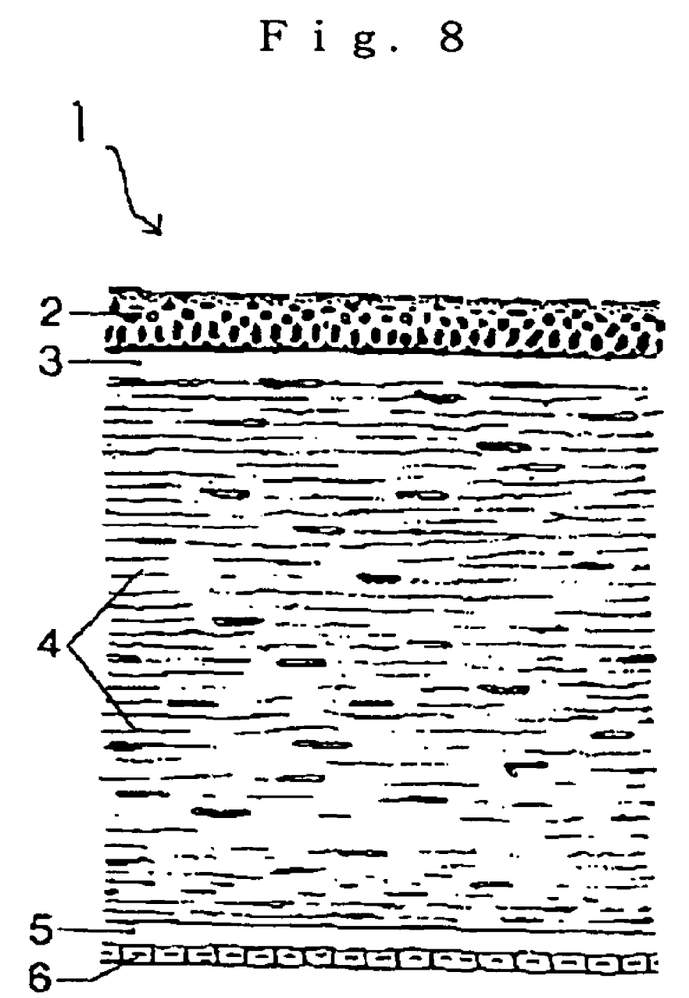
FIG. 8 Graphical cross section of cornea.

As shown in FIG. 8, the cornea 1 is comprised of a multi-layered structure: the anterior corneal epithelium 2, Bowman's membrane 3, the corneal stroma 4, Descemet's membrane 5, and the corneal endothelial cells 6. When preserved over time, the corneal epithelial cells are left out, the corneal stroma swell, and the endothelial cells decrease. Concerning to the corneal epithelial cells and the stromal cells, these are not problem because of their ability to regenerate. However, as stated above, the CECs have a poor ability to proliferate, so that when the cornea is stored for an extended period, there is a problem in that the endothelial cells decrease. That is, in the case of a cornea is transplanted, the method of storage may lead to a problem in decrease of endothelial cells.

Thus, there is a problem in that the CECs have an extremely poor ability to proliferate within the organism. Accordingly, in an attempt to regenerate CECs having an extremely poor ability to proliferate within the organism, a method of reconstructing the cornea has been proposed in which cultured CECs are planted on the corneal stroma from which endothelial cells have been removed, and a layer of CECs is built on the stroma (Japanese Unexamined Patent Publication (KOKAI) No. 2002-78723).

However, since the above-described method presents problems in that it requires a cornea from which the endothelial cells have been removed, the method does not provide a solution for a shortage of cornea donors, and for an inability to handle the rejection accompanying a transplant. Further, it is possible to remove the cornea of the patient for a certain period so that a corneal endothelial cell layer can be rebuilt on the cornea. However, while the corneal endothelial cell layer is being reconstructed, the patient must do without sight and is greatly burdened in his daily life.

Accordingly, the object of the present invention is to solve these problems by providing a laminate of implantable cultured endothelial cells layer.

DISCLOSURE OF THE INVENTION

The present invention solving the above-described problems is as follows:

(1) A laminate comprising a transparent type I collagen sheet and a cultured layer of human corneal endothelial cells provided on said sheet.

(2) The laminate according to (1) wherein the transparency of said transparent type I collagen sheet is maintained under physiological conditions.

(3) The laminate according to (1) or (2) wherein said transparent type I collagen sheet has an adhesive factor or bioadhesive layer on the opposite side from the cultured layer of human corneal endothelial cells.

(4) The laminate according to any of (1) to (3) wherein an adhesive factor or bioadhesive layer is provided between said transparent type I collagen sheet and said cultured layer of human corneal endothelial cells.

(5) The laminate according to (3) or (4) wherein said adhesive factor is human plasma fibronectin.

(6) A method for manufacturing a laminate of human corneal endothelial cells layer comprising:
preparing a transparent type I collagen sheet; and
culturing human corneal endothelial cells on said sheet to form a cultured layer of human corneal endothelial cells.

(7) The method according to (6) wherein the transparency of said transparent type I collagen sheet is maintained under physiological conditions.

(8) The method according to (6) or (7) wherein said human corneal endothelial cells are cultured on a transparent type I collagen sheet that has been coated with an adhesive factor or a bioadhesive.

(9) The method according to (8) wherein said adhesive factor is human plasma fibronectin.

(10) The method according to any of (6) to (9) wherein said human corneal endothelial cells are cultured by providing a culture solution containing human corneal endothelial cells on a transparent type I collagen sheet and applying centrifugal force in the direction of said transparent type I collagen sheet.

(11) The method according to any of (6) to (10) wherein in the culturing of said human corneal endothelial cells, the concentration of said human corneal endothelial cells in a culture solution is set to within a range of from $1 \times 10^5$ to $1 \times 10^7$ cells /mL.

(12) The method according to any of (6) to (11) wherein said corneal endothelial cells are cells that have been passaged.

(13) The method according to (12) wherein the passage is conducted for 2 to 10 generations.

(14) The method according to any of (6) to (13) wherein said corneal endothelial cells are cultured under conditions of 37° C. and 10 percent $CO_2$.

(15) The method according to any of (6) to (14) wherein the culturing is conducted using a cell culturing solution comprising fetal bovine serum, growth factor, and hyaluronic acid in a medium of low glucose concentration.

The present invention provides a laminate of implantable cultured endothelial cells layer.

BEST MODES OF IMPLEMENTING THE INVENTION

The present invention relates to a laminate of cultured human corneal endothelial cells (HCECs) layer comprised of a transparent type I collagen sheet and a cultured layer of HCECs provided on this sheet.

The transparent type I collagen sheet constituting the laminate of the present invention is a material that can maintain its transparency under physiological conditions (neutral pH). Here, the term "transparency" means transparency of a degree that does not cause problems with vision when the laminate of the present invention is implanted.

The thickness of the transparent type I collagen sheet is not specifically limited; when implantation is considered, a thickness ranging from 5 to 500 micrometers suffices. When implanting only the vicinity of the corneal endothelium, a thickness ranging from 5 to 50 micrometers is suitable.

Any transparent type I collagen sheet made from a starting material of soluble collagen satisfying the following conditions may be employed: (1) alkali-soluble collagens (for example, see Hattori S., Adachi E., Ebahara T., Shirai T., Someki I., Irie S., *J. Biochem.* 1999; 125: 676-684); collagens with an isoelectric point of about pH 4, such as chemically modified collagens; (2) collagens with an isoelectric point of about pH 9, such as acid-soluble collagens and enzyme-soluble collagens, to which a substance inhibiting the formation of fiber (for example, glucose, sucrose, and arginine) has been admixed.

The transparent type I collagen sheet can be formed by causing a collagen solution to flow onto a casting mold such as an acrylic sheet and drying. The casting mold may be flat or concave.

The transparent type I collagen sheet may be in the form of a solution or a molded collagen sheet that has been crosslinked. Crosslinking may be conducted by a physical crosslinking method such as irradiation with UV or gamma rays, or a chemical crosslinking method employing a condensing agent such as a water-soluble carbodiimide. A collagen sheet of desired thickness may be obtained by varying the crosslinking method, concentration of condensing agent, processing time, reaction temperature, and the like.

The laminate of the present invention may have a layer of adhesive factor or bioadhesive on the opposite side from the cultured layer of HCECs on the transparent type I collagen sheet. Having a layer of adhesive factor or bioadhesive on the opposite side from the cultured layer of HCECs on the transparent type I collagen sheet promotes adhesion of the laminate of the present invention to the corneal stroma during implant.

The laminate of the present invention may also have a layer of adhesive factor or bioadhesive between the transparent type I collagen sheet and the cultured layer of HCECs. Having a layer of adhesive factor or bioadhesive between the transparent type I collagen sheet and the cultured layer of HCECs promotes adhesion between the transparent type I collagen sheet and the cultured layer of HCECs.

The adhesive factor and bioadhesive need only be compounds that do not affect the organism once the laminate of the present invention has been implanted into the eye. Examples of bioadhesives are fibrin pastes; examples of adhesive factors are human plasma fibronectin and laminin.

The method for manufacturing the laminate of the present invention will be described below.

As set forth above, the method for manufacturing a laminate of the present invention comprises the steps of preparing a transparent type I collagen sheet and culturing HCECs on this sheet to form a cultured layer of HCECs. The transparent type I collagen sheet may be coated with adhesive factor or bioadhesive. The HCECs that are cultured may be obtained by the method described in Unexamined Japanese Patent Publication (KOKAI) No. 2002-78723.

From the perspective of the density of the HCECs, the HCECs are cultured after providing a culture solution containing HCECs on a transparent type I collagen sheet and applying centrifugal force in the direction of the transparent type I collagen sheet. A centrifugal force ranging from 500 to 2,000 rpm, for example, is desirable.

When culturing HCECs on a collagen sheet, the concentration of the HCECs in the culture solution can be set to within a range from $1\times10^5$ to $1\times10^7$ cells /mL. Within this range, the cells on the collagen achieve adequate density (become confluent) within 2 to 3 days after inoculation.

Multiple generations of the CECs are subcultured. The number of generations is desirably 2 to 10. The subcultured cells may be frozen and stored until cultured on a collagen sheet. Cells that are kept in frozen storage are thawed out and then employed in culturing.

The CECs are cultured on a collagen sheet under, for example, conditions of 37° C. and 10 percent $CO_2$. They may also be cultured using a cell culture solution comprising fetal bovine serum, growth factor, and hyaluronic acid in a medium of low glucose concentration.

The D-MEM, MEM, and the like commonly employed in the culturing of animal cells are examples of cell culture solutions that may be employed. Preferably, 5 to 15 percent fetal bovine serum (FBS), growth factor, and the like are incorporated into a medium (D-MEM or the like) of low glucose concentration. Here, the glucose concentration in the medium is lower than the glucose concentration commonly employed: 2.0 g/L or less; for example, 0.1 to 2.0 g/L, preferably 0.1 to 1.0 g/L. Examples of growth factor are B cell growth factor (BCGF), epidermal growth factor (EGF), recombinant EGF (rEGF), and fibroblast growth factor (FGF). One or multiple factors may be suitably combined and incorporated into the medium. The concentration of these growth factors in the medium is 1 to 5 ng/mL, preferably 1 to 2 ng/mL. In addition to the above-described medium composition, preservatives such as doxycycline and antifungal agents such as Fungizone may be added. Hyaluronic acid (sodium hyaluronate) may be added in a proportion of about 1.0 to 3.0 percent, preferably 1.0 to 2.0 percent.

The culture temperature is 35 to 38° C., preferably 37° C. Culturing is conducted in an incubator at a humidity of 90 to 100 percent (preferably 100 percent) with 5 to 15 percent $CO_2$ (preferably 10 percent $CO_2$). The cells are cultured until they reach a dense state (about 1 to 5 days under normal conditions).

The number of cells dripped onto the collagen sheet is desirably two or more times the normal density of endothelial cells (3,000 cells/mm$^2$), with twice (6,000 cells/mm$^2$) to 10 times (60,000 cells/mm$^2$) being preferred.

EXAMPLES

The present invention is further described below in view of examples.

[Media and Culture Conditions for HCECs]

All the primary cultures and serial passages of HCECs were done in growth medium consisting of low-glucose Dulbecco's modified Eagle's medium (DMEM) supplemented with 15% fetal bovine serum (FBS), 2.5 mg/L fungizone (Gibco BRL, Grand Island, N.Y.), 2.5 mg/L doxycycline, and 2 ng/mL basic fibroblast growth factor (bFGF; Sigma, St. Louis, Mo.). Cells were maintained in a humidified incubator at 37° C. and 10% $CO_2$. Medium used to produce bovine extracellular matrix (ECM) consisted of low-glucose DMEM with 10% FBS, 5% calf serum (Gibco BRL), 2.5 mg/L fungizone, 2.5 mg/L doxycycline, 2 ng/mL bFGF, and 2% dextran (Sigma). Media for the HCEC and bovine CEC cultures were changed every 2-3 days.

[Primary Culture of HCECs]

Primary HCEC cultures were made as described elsewhere (Miyata K, Drake J, Osakabe Y, et al. *Cornea.* 2001;20:59-63). Briefly, cultures were established from the remainder of donor corneas after full-thickness corneal transplantation. All the donor corneas were obtained from the Rocky Mountain Lions' Eye Bank. Small explants from the endothelial layer, including Descemet's membrane, were removed with sterile surgical forceps. The approximately 200 explants per cornea were placed endothelial cell-side down onto four 35-mm tissue culture dishes coated with bovine ECM and the dishes carefully placed in an incubator. The medium was exchanged after 3 days and thereafter replaced every other day. When a sufficient proliferating cell density was reached, the HCECs were passaged at ratios ranging from 1:1 to 1:4. Subsequent passages were done by the same method, but at a ratio of 1:16. Cultured cells from the fourth and fifth passages were used in the study.

[Seeding of Cultured HCECs on Collagen Sheets]

The cell carriers were collagen sheets obtained from Nippi Research Institute of Biomatrix (Tokyo, Japan). The collagen sheets were those with 15 μm thick in dried states and obtained by applying 12 g of alkali soluble collage in 0.5% concentration prepared sterilely from pig skin on an alkylic plate (5 cm×7.5 cm), drying in a clean bench and then irradiating ultraviolet light to each surface for 30 minute respectively. Each sheet is composed of a network of loosely cross-linked type I collagen (for examples, Stenzel K H, Dunn M W, Rubin A L, Miyata T. *Science.* 1969;164:1282-1283).

Figure 1:
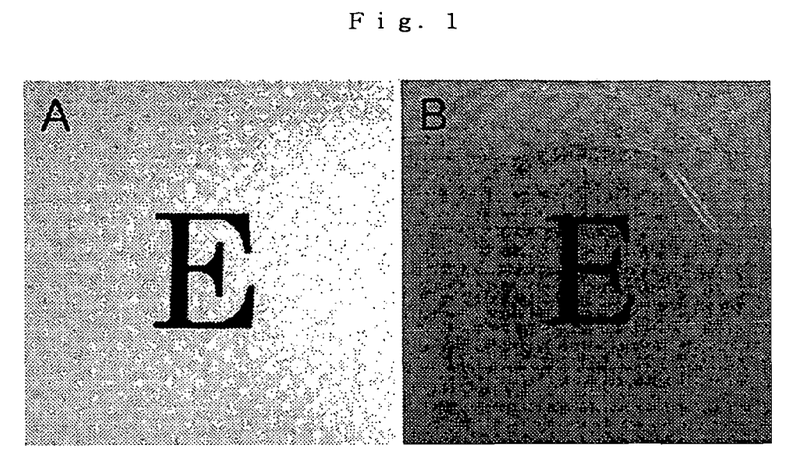
FIG. 1 Showing transparency of cultured HCEC collagen sheet. The letter "E" is clearly visible through the HCEC sheet. (A) is the letter "E" without the HCEC sheet and (B) is the letter "E" with the HCEC sheet.

Before use, the desiccated sheets were immersed for 10 minutes in sterilized saline (FIG. 1A). A 6.0-mm trephine was used as the biopsy punch (Kai Medical, Gifu, Japan). Each sheet was approximately 40 to 50 μm thick. To observe HCEC localization after transplantation, cultured HCECs were labeled with Cell tracker CM-DiI (C-7000; Molecular Probes, Oreg.) before reconstruction. Immediately before labeling, CM-DiI was diluted to 10 μg/mL with phosphate-buffered saline (PBS). Trypsinized $1.0 \times 10^6$ HCECs were incubated in 5 mL CM-DiI solution on ice for 5 minutes at 37° C. and then for an additional 15minutes at 4° C. After labeling, the HCECs were washed twice with PBS and resuspended in 300 μL low-glucose DMEM containing 6% dextran (Amersham Pharmacia Biotech AB, Uppsala, Sweden).

Next, the collagen sheets were coated with 1.0 μg/mm$^2$ human plasma fibronectin (Gibco BRL). An HCEC suspension of $1.0 \times 10^6$ cells in 300 μL culture medium was transferred to each sheet, and the sheet placed in individual wells of 96-well plates. The plates then were centrifuged at 1000 rpm (176 g) for 10 minutes to enhance cell attachment to the sheets. Sheets were maintained in the cell culture medium for 2 days, after which nonadhering cells and debris were removed. The letter "E" was clearly visible through each HCEC cultured layer on the sheet, indicative of transparency (FIG. 1B).

[Measurement of the Pump Function of the HCEC Collagen Sheet]

Pump functions of four HCEC collagen sheets were measured, with some modification, in a Ussing chamber as reported previously (Hodson S, Wigham C. *J Physiol.* 1983; 342:409-419; Wigham C, Hodson S. *Curr Eye Res.* 1981;1: 37-41; Wigham C G, Turner H C, Swan J, Hodson S A. *Pflugers Arch.* 2000;440:866-870). Six relaxing radial incisions were made in the peripheral area of donor corneas from which epithelium had been scraped mechanically. The donor corneas (n=4), collagen sheets only (n=4), and HCEC collagen sheets (n=4) were mounted in the Ussing chamber. Corneas were incubated in Ringer solution containing (in mM): NaCl, 117.5; NaHCO$_3$, 24; KCl, 4; Na$_2$HPO$_4$, 1; MgSO$_4$, 1; glucose, 4.45; reduced glutathione, 1; and CaCl$_2$, 2.54 and bubbled with a 5% CO$_2$-7% O$_2$, 88% N$_2$ gas mixture to pH 7.38. After steady state levels of the potential difference and short-circuit current were reached, ouabain (0.1 mM), an Na$^+$,K$^+$-ATPase inhibitor, was added to the chamber, and the potential difference and short-circuit current redetermined.

[Transplantation of Cultured HCECs into Rabbits]

Figure 3:
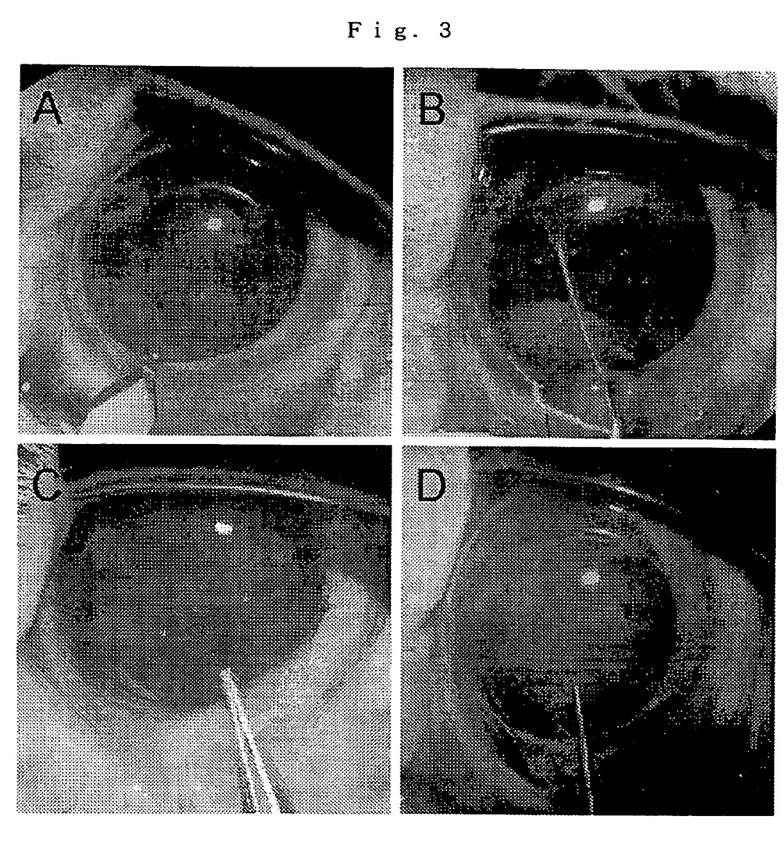
Figure 4:
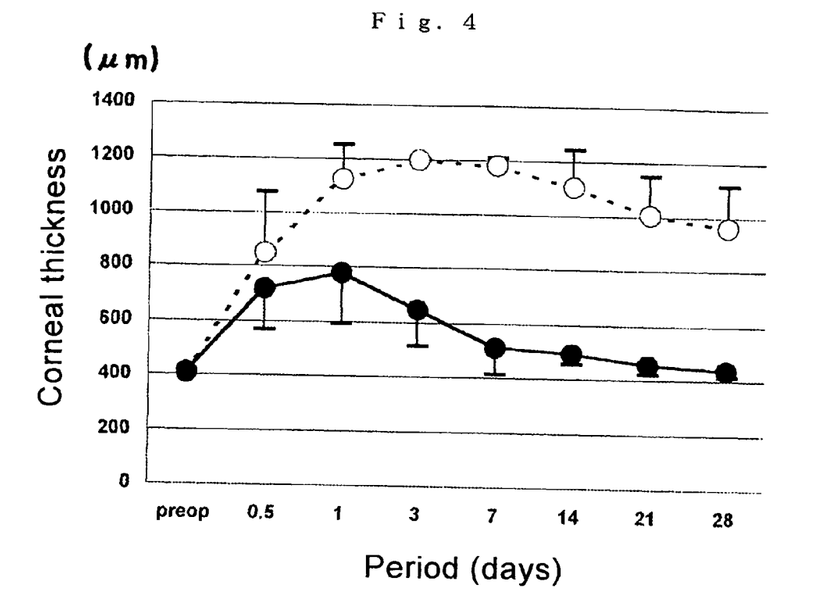
FIG. 4 Central corneal thickness in the control (open circles) and HCEC (closed circles) groups. In the control group, mean corneal thickness remained approximately 1000 μm throughout the 28-day observation period. In contrast, mean corneal thickness in the HCEC group gradually decreased, becoming significantly less than that in the control group. There are significant differences in corneal thickness (*$P<0.05$, **$P<0.01$, †$P<0.001$) between the HCECs and control group on days 1, 3, 7, 14, 21, and 28.

Treatment was in accordance with the ARVO Statement for the Use of Animals in Ophthalmic and Vision Research. All the rabbits were from Saitama Experimental Animals, Inc. (Saitama, Japan). Eight New Zealand White rabbits, weighing 2.0 to 2.4 kg, were anesthetized intramuscularly with ketamine hydrochloride (60 mg/kg; Sankyo, Tokyo, Japan) and xylazine (10 mg/kg, Bayer, Munich, Germany). After disinfection and sterile draping of the operation site, a 6-mm sclerocorneal incision centered at 12 o'clock was made with a slit knife (Alcon Surgical, Tokyo, Japan), and a viscoelastic agent (Healon; Amersham Pharmacia Biotech AB) was infused into the anterior chamber (FIG. 3A). After the corneal surface had been ruled with a marking pen (Devon Industries Inc, Madrid, Spain), a 6.0-mm diameter circular Descemetorhexis was created in the center of the cornea with a 30-gauge needle (Terumo, Tokyo, Japan) (FIG. 3B), and Descemet's membrane was removed from the anterior chamber of the eye (FIG. 3C). A reconstructed HCEC sheet with a drop of 1.0 μg/μL fibronectin was brought into the anterior chamber forceps and attached and fixed to the posterior stroma stripped of Descemet's membrane (FIG. 3D). Adhesion of the reconstructed HCEC sheet to the recipient stroma was confirmed after the anterior chamber was washed with PBS three times. If the HCEC sheet was difficult to attach, an air bubble was injected into the anterior chamber. The sclerocorneal wound was closed with two to three interrupted 10-0 nylon sutures (Mani, Tochigi, Japan), and of loxacin ophthalmic ointment (Santen, Osaka, Japan) was instilled immediately after.

The rabbits were divided into two groups: the HCECs (rabbits with peeled off Descemet's membrane and cultured HCEC transplants on a collagen sheet) and control (rabbits with peeled off Descemet's membrane but no transplantation). Each group comprised four eyes from four rabbits. No immunosuppressive agents were administered topically or systemically during the follow-up period.

[Clinical Observations]

Each surgically treated eye was checked daily by external examination with a slit lamp biomicroscope and photographed 7, 14, and 28 days after surgery. Central corneal thickness was measured with an ultrasound pachymeter (Tomey, Nagoya, Japan), and intraocular pressure with a pneumatic tonometer (model 30 Classic; Mentor O&O, Norwell, Mass.) 1, 3, 7, 14, 21, and 28 days after surgery. An average of three readings was taken.

[Histologic Examination and Localization of HCECs]

One month after transplantation, the rabbits, under deep anesthesia, were killed by an intravenous overdose of pentobarbital sodium (Dainippon Pharmaceutical, Osaka, Japan). Their corneas were excised and bisected. HCEC morphology was evaluated on one side of the divided corneas. All the plates were examined under a light microscope (model BX-50; Olympus, Tokyo, Japan) and the images saved to a personal computer. The number of cells in a 0.1 mm×0.1 mm area was counted at four different sites in the four reconstructed corneas. Wholemount samples of the corneas of the HCEC group also were examined for DiI-labeled HCEC fluorescence under a fluorescence microscope (models BH2-RFL-T3 and BX50; Olympus, Tokyo, Japan) at an excitation wavelength of 420 nm and an emission wavelength of 480 nm. They next were immersed in fixative consisting of 4% paraformaldehyde (Wako) in 0.1 M PBS at pH 7.4, then embedded in OCT compound at −20° C. The frozen OCT-embedded sections were cut 8-μm thick, and the slices placed on microscope slides, after which DiI-labeled HCEC fluorescence was checked under the fluorescein microscope.

The other half of the divided cornea was removed immediately, fixed in 10% formalin (Wako). Sectioned samples were embedded in OCT compound (Tissue-Tek®, Miles Laboratories, Naperille, Ill.) and kept at −20° C. The frozen sections were cut 8-μm thick, the slices placed on Silane-coated microscope slides (Muto Pure Chemicals, Tokyo, Japan), stained with hematoxylin and eosin (HE), and observed under a light microscope.

[Statistics]

A one-way analysis of variance and Scheffe's multiple comparison were used for potential difference and short circuit current measurements. The unpaired t-test was used to compare the mean values of corneal thickness. All analyses were made with a Stal View statistical software package (Abacus Concepts, Berkeley, Calif.).

[Pump Function of the HCEC Sheet]

Figure 2:
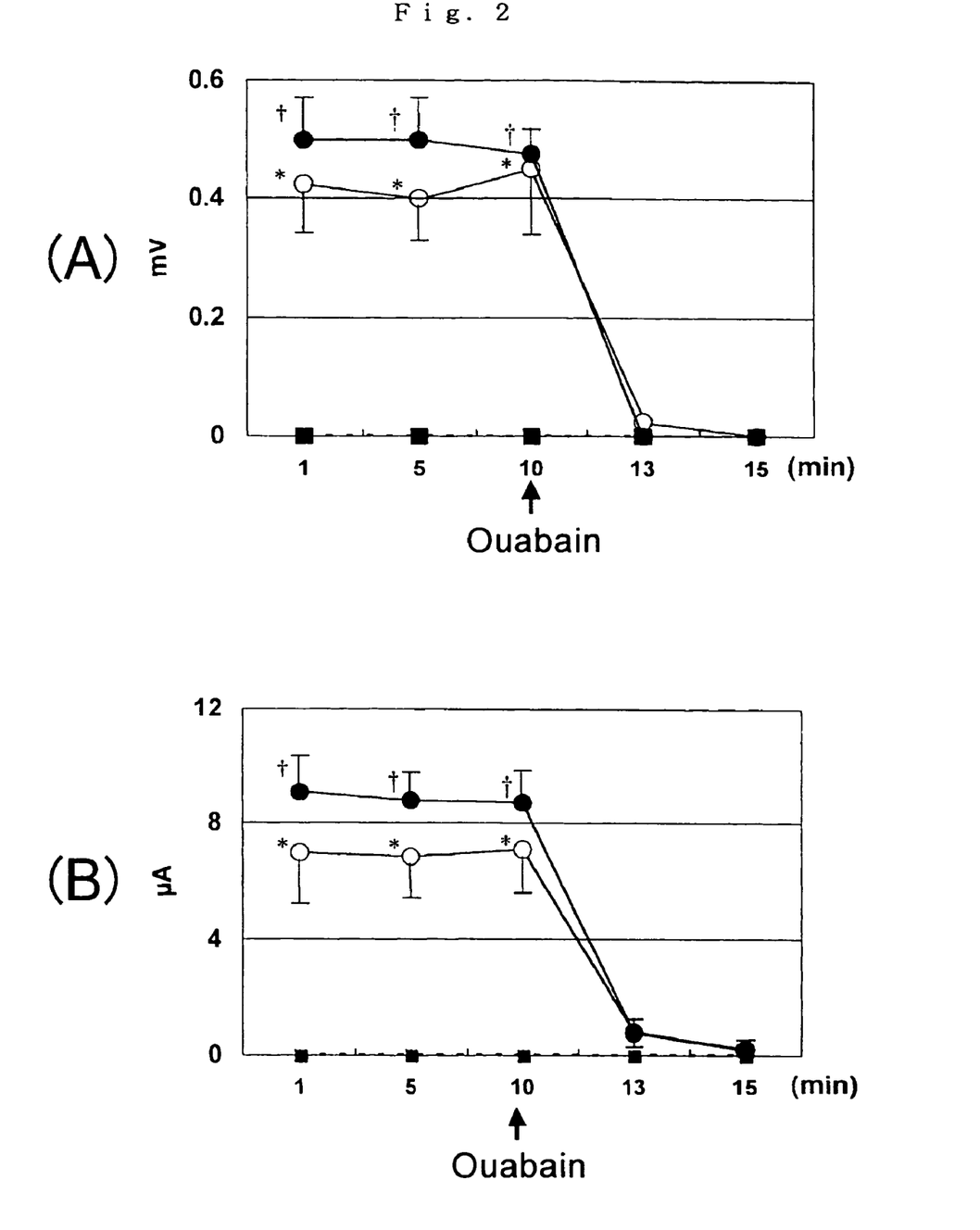

Time-course changes in the average and standard deviation (SD) of the differences in potential differences in the donor corneas and in the HCEC collagen sheets, are shown in FIG. 2A (collagen sheet and corneal stromal sides, positive). Average potential differences in the HCEC collagen sheets 1, 5, and 10 minutes after measurement were 85%, 80%, and 95% of the value for human donor corneas deprived of epithelia. The potential difference for the collagens sheets only (FIG. 2A) and for human donor corneas deprived of the epithelium and endothelium (data not shown) was 0 mV at each time point. After the $Na^+,K^+$-ATPase inhibitor ouabain was added to the chambers, within 5 minutes the potential difference became 0 mV in all the test samples.

The average and standard deviations of the short-circuit current in the donor corneas, collagen sheet, and HCEC collagen sheet are shown in FIG. 2B. The average short-circuit current in the HCEC collagen sheets 1, 5, and 10 minutes after measurement was 76%, 78%, and 82% that of the human donor corneas deprived of their epithelia. The short-circuit currents of the collagen sheets and human donor corneas deprived of the epithelium and endothelium was 0 μA at each time point. After ouabain was added to the chambers, within 5 minutes the short-circuit current became 0 μA in all the test samples.

[Clinical Observations after Surgery]

Figure 5:
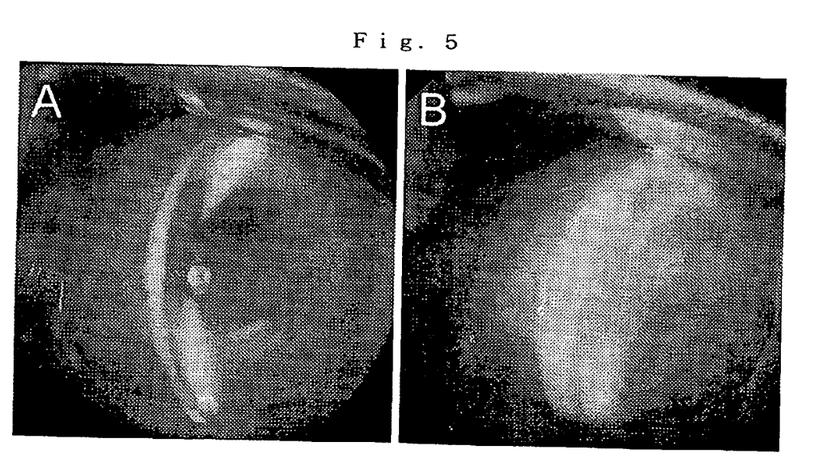
FIG. 5 Anterior segment photographs made with a slit lamp microscope 28 days after surgery. (A) Representative photograph of an anterior segment in the HCEC group showing a thin cornea without stromal edema. The pupil margin is clearly visible. (B) Marked corneal edema was present in the control group photograph. No details of the anterior chamber are visible.

Corneal edema decreased much earlier after HCEC sheet transplantation in the HCECs than in the control group. In the control group, mean corneal thickness was approximately 1000 μm throughout the 28 days of observation. In contrast, it decreased rapidly in the HCEC group, being significantly less than in the control group 1 ($P<0.05$), 3 ($P<0.01$), 7, 14, 21, and 28 days ($P<0.001$) after surgery. FIG. 5 shows representative anterior segment photographs for each group. Compared with the opaque cornea with severe stromal edema seen in the control group, in the HCEC group on day 28, the reconstructed cornea transplanted by means of a cultured HCEC sheet was clear with no stromal edema. In the slit lamp examination, mild stromal opacity was discernible on the layer attached to the collagen sheet. There was no intraocular pressure increase in each group throughout the observation period. Reconstructed corneas transplanted only with a collagen sheet had marked corneal edema with opacity, consistent with the findings for the anterior segment in the control group (data not shown).

[Evaluation of HCECs in Reconstructed Corneas Receiving a Cultured HCEC Sheet Transplant]

Figure 6:
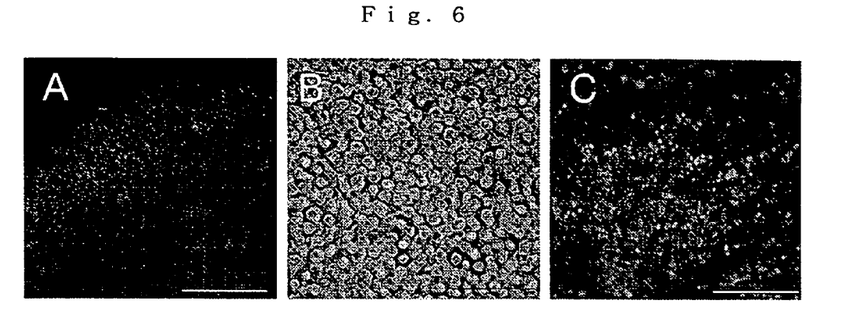
FIG. 6 Fluorescence microscopy of a cornea in the DiI-labeled HCEC group on day 28. Fluorescein microscopy (A, C) and a bright-field micrograph (B) in the HCEC group of cornea flatmounts, 28 days after transplantation. (A) DiI-positive cells formed a clear margin on the transplanted HCEC collagen sheet. (B) At high magnification, HCECs on the collagen sheet maintained regular cell form and confluence. (C) Most cells on the collagen sheet were DiI-positive at the same magnification as in (B). Bar (A), 1000 μm. Bars (B, C), 100 μm.

A fluorescence microscope examination of wholemount corneas showed DiI-positive cells localized on the collagen sheet and a clear margin on the transplanted HCEC sheet 28 days after transplantation (FIG. 6A). As shown in FIG. 6B, HCECs on the collagen sheets had quasiregular forms with well-defined cell boundaries. No cell defects were apparent on the collagen sheets. Most cells on a collagen sheet were DiI-positive on the posterior surface of the corneas (FIG. 6C). The findings were similar for the other three corneas of the HCEC group. Endothelial densities of the four grafts in the HCEC group 28 days after surgery ranged from 2325 to 2900 cells/mm$^2$ (mean±SD, 2531±290 cells/mm$^2$). In the control group, no CECs were present on stroma on which Descemetorhexis had been performed (data not shown).

[Histologic Examination]

Figure 7:
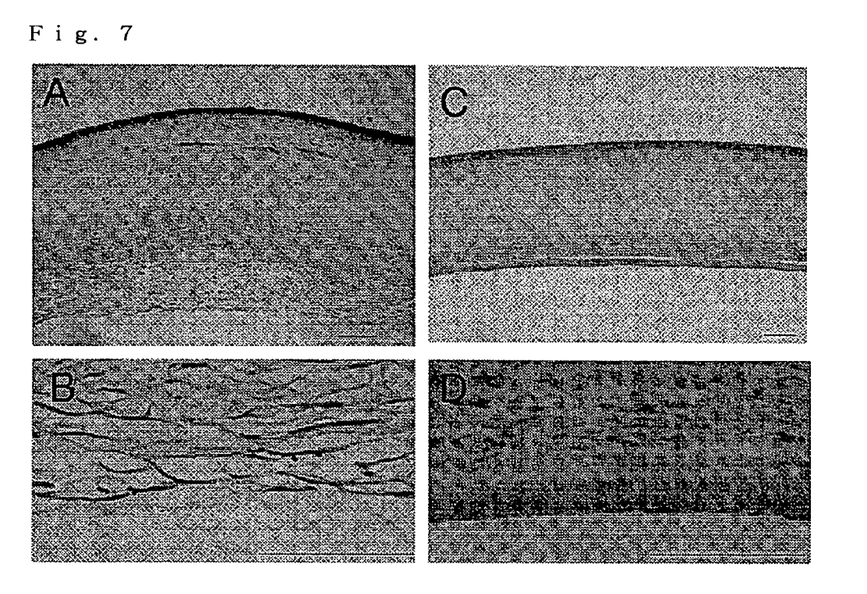
FIG. 7 Histologic cornea examination 28 days after HCEC transplantation. (A, B) The control group, in which HCEC and Descemet's membrane are absent, shows marked stromal edema and diffuse cell infiltration. (C, D) HE staining showing the presence of a collagen sheet with HCECs on the posterior surface of the cornea and no stromal edema in the HCEC group. Fibroblast-like cells are present in the posterior corneal stroma attached to the collagen sheet. Bar, 100 μm.

HE-stained sections 28 days after transplantation are shown in FIG. 7. Stromal edema and diffuse cell infiltration into the stroma were present in the control group (FIG. 7A). In the posterior corneal stroma without Descemet's membrane, there was marked edema (FIG. 7B). In contrast, histologic findings for the HCEC group show no apparent stromal edema on the collagen sheet (FIG. 7C). Corneal thickness in the HCEC group was clearly less than in the control group. As shown in FIG. 7D, an HCEC monolayer was present on the posterior surface of the collagen sheet. Fibroblast-like cells can be seen in the posterior stroma attached to the collagen sheet in the HCEC group (FIG. 7D). Similar findings were obtained for the posterior stroma of reconstructed corneas transplanted with a collagen sheet without HCEC (date not shown).

[DISCUSSION]

Full-thickness corneal transplantation has been performed clinically for such CEC diseases as Fuchs dystrophy and pseudophakic or aphakic bullous keratopathy. This technique, however, has the severe complications associated with open-sky surgery as well as frequent complications of high or irregular astigmatism, refractive error, and suture-related problems. Deep lamellar endothelial keratoplasty (DLEK), which is the replacement of the posterior corneal layer with a graft consisting of the posterior stroma, Descemet's membrane, and CECs, has been used to treat endothelial dysfunction. Moreover, Melles et al. have introduced a surgical technique for transplanting Descemet's membrane derived from donor cornea ex vivo. DLEK and Descemet's membrane transplantation solve the problems that accompany corneal surface circular incision and suturing. These techniques use human donor cornea, but worldwide there is a problem of an inadequate supply of donor corneas.

To make up for the inadequate supply of donor corneas, studies have shown the feasibility of using cultured animal CECs as transplants in in vivo animal models. This type of transplantation, however, has yet to be achieved clinically because of difficulties in culturing HCECs from adult human donor corneas and the lack of thin, transparent HCEC carriers. We found that the potential difference and short-circuit current of a cultured HCEC collagen sheet are similar to those of donor corneas, indicative that the pump function, which depends mainly on $Na^+$, $K^+$-ATPase, and does not work completely, is satisfactory in reconstructed HCEC sheets. Rabbit corneas receiving cultured HCEC collagen sheets showed decreased corneal edema, whereas severe stromal edema was present throughout the follow-up period in corneas without cultured HCEC sheets. Results are supported by histologic examinations of corneas, with and without collagen sheet bearing cultured HCECs. These findings and the residual DiI-labeled cells derived from HCECs indicate that transplantation of the cultured HCECs on the collagen sheet contributes to the maintenance of corneal stromal hydration and transparency, evidence of the feasibility of using this type of transplantation as a substitute carrier of Descemet's membrane.

Histologic examinations showed fibroblast-like cells at the stroma attached to the HCEC collagen sheets. These cells were induced by the collagen sheets with fibronectin as the adhesive, not by the cultured HCECs, as seen in similar histologic findings for the transplantation of collagen sheets without HCECs. Because the HCEC sheet produced only mild opacity of the posterior stromal layer attached to the collagen sheet in the slit lamp microscope examination and no immunosuppressive agents had been administered during the follow-up period, topical immunosuppressants such as corticosteroid eye drops may easily prevent fibroblast-like cell infiltration. However, long-term follow-up studies are needed.

It is worth commenting on the immunologic rejection of human-to-rabbit xenotransplantation that occurs in this model. In the full-thickness murine corneal xenotransplantation model, no hyperacute rejection occurs, but corneal xenografts are rejected in concordant or discordant combination without exception, on the average over a period of 2 to 16 days after transplantation. In our study, no apparent inflammatory reactions, such as massive cell infiltration, keratic precipitates, or fibrin formation were present in the anterior chamber of rabbit eye under slit lamp microscopy and human DiI-labeled CEC showed no apparent cell loss, evidence that there was no notable episode of acute immunologic rejection. The anterior chamber of the eye is an immune-privileged site and anterior chamber-associated immune deviation (ACAID) permits the long-term acceptance and survival of histoincompatible tissue grafts that otherwise are rejected when transplanted to various anatomic sites. In HCEC sheet transplantation, the transplanted HCECs, which face the anterior chamber, may induce ACAID, thereby avoiding immunologic rejection, the leading cause of graft failure in full-thickness corneal transplantation.

In summary, using anterior chamber insertion of a collagen sheet bearing HCECs, we developed a transplantation technique that uses a collagen sheet as the substitute carrier of HCECs. We conclude that (1) cultured HCECs derived from adult human donor corneas retain the essential CEC function of dehydration of the corneal stroma in vivo; (2) an artificial collagen sheet can serve as the carrier of HCECs; and (3) anterior chamber insertion of an HCEC collagen sheet with fine forceps does not require a corneal surface incision and sutures. Our findings indicate that transplantation of cultured HCECs by means of a collagen sheet is a feasible technique for use with eyes that have CEC dysfunction only.

INDUSTRIAL APPLICABILITY

A laminate of cultured HCECs layer and a method for manufacturing the same of the present invention provide implantable cultured endothelial cells.

BRIEF DESCRIPTION OF THE DRAWINGS

FIG. 2 Time-course changes in the potential difference and short-circuit current in a cultured HCEC collagen sheet. (A) The average potential difference of the HCECs was 80% to 95% that of human epithelium-deprived donor corneas. Addition of ouabain, an $Na^+$, $K^+$-ATPase inhibitor, produced a short-circuit current of 0 mA in all the samples. (B) The average short-circuit current of the HCECs was 76% to 82% that of human epithelium-deprived donor corneas. Addition of ouabain produced a short-circuit current of 0 μA in all the samples tested. Closed and open circles, and closed squares respectively indicate human epithelium-deprived donor corneas (n=4), HCEC sheets (n=4), and collagen-only sheets (n=4). Data are the mean±SD. *$p<0.001$, HCEC sheet vs. collagen sheet; † $p<0.001$, human donor cornea vs. collagen sheet FIG. 3 Surgical procedure for HCEC sheet transplantation. (A) A 6-mm sclerocorneal incision made with a slit knife was centered at 12 o'clock. (B) A 6.0-mm diameter circular Descemetorhexis was performed with a 30-gauge needle. (C) Descemet's membrane was removed from the anterior chamber of the eye. (D) The reconstructed HCEC sheet was brought into the anterior chamber and attached to the posterior stroma.

The invention claimed is:

1. A laminate comprising a transparent type I collagen sheet that has been coated with an adhesive factor or a bioadhesive and a cultured layer of human corneal endothelial cells provided on said sheet, wherein said sheet has a thickness ranging from 5 to 50 micrometers.

2. The laminate according to claim 1, wherein the transparency of said transparent type I collagen sheet is maintained under physiological conditions.

3. The laminate according to claim 1, wherein said adhesive factor or bioadhesive layer is on the opposite side from the cultured layer of human corneal endothelial cells.

4. The laminate according to claim 3, wherein said adhesive factor or bioadhesive layer is provided between said transparent type I collagen sheet and said cultured layer of human corneal endothelial cells.

5. The laminate according to claim 3, wherein said adhesive factor is human plasma fibronectin.

6. A method for manufacturing a laminate of a cultured layer of human corneal endothelial cells on a transparent type I collagen sheet comprising:
  preparing a transparent type I collagen sheet having a thickness ranging from 5 to 50 micrometers ; and
  culturing a solution containing human corneal endothelial cells on said sheet to form a laminate comprising a cultured layer of human corneal endothelial cells and said transparent type I collagen sheet having a thickness ranging from 5 to 50 micrometers.

7. The method according to claim 6 wherein the transparency of said transparent type I collagen sheet is maintained under physiological conditions.

8. The method according to claim 6, wherein said human corneal endothelial cells are cultured on said transparent type I collagen sheet that has been coated with an adhesive factor or a bioadhesive.

9. The method according to claim 8, wherein said adhesive factor is human plasma fibronectin.

10. The method according to claim 6, wherein said human corneal endothelial cells are cultured after providing the solution containing human corneal endothelial cells on the transparent type I collagen sheet and applying centrifugal force in the direction of said transparent type I collagen sheet.

11. The method according to claim 6, wherein in the culturing of said human corneal endothelial cells, the concentration of said human corneal endothelial cells in the solution is set to within a range of from $1 \times 10^5$ to $1 \times 10^7$ cells/mL.

12. The method according to claim 6, wherein said corneal endothelial cells are cells that have been passaged.

13. The method according to claim 12, wherein the passage is conducted for 2 to 10 generations.

14. The method according to claim 6, wherein said corneal endothelial cells are cultured under conditions of 37° C. and 10 percent $CO_2$.

15. The method according to claim 6, wherein the culturing is conducted using a cell culturing solution comprising fetal bovine serum, growth factor, and hyaluronic acid in a medium of low glucose concentration.

16. A method of transplanting a laminate comprising a transparent type I collagen sheet ranging from 5 to 50 micrometers in thickness and a cultured layer of human corneal endothelial cells provided on said sheet into the anterior chamber of an eye from which the Descemet's membrane was removed, the method comprising adding fibronectin to said laminate and inserting the laminate into the anterior chamber.

17. The method according to claim 16, wherein the inserted laminate is attached and fixed to the posterior corneal stroma.

* * * * *